US010300175B2

(12) United States Patent
Wise et al.

(10) Patent No.: US 10,300,175 B2
(45) Date of Patent: May 28, 2019

(54) MEDICAL DEVICES WITH REDUCED THROMBOGENICITY

(71) Applicant: The Heart Research Institute Ltd., Newton (AU)

(72) Inventors: Steven G. Wise, Sydney (AU); Martin K. C. Ng, New South Wales (AU)

(73) Assignee: Heart Research Institute, Ltd., Newton (AU)

( * ) Notice: Subject to any disclaimer, the term of this patent is extended or adjusted under 35 U.S.C. 154(b) by 472 days.

(21) Appl. No.: 14/851,251

(22) Filed: Sep. 11, 2015

(65) Prior Publication Data

US 2016/0074563 A1    Mar. 17, 2016

Related U.S. Application Data

(60) Provisional application No. 62/049,879, filed on Sep. 12, 2014.

(51) Int. Cl.
*A61F 2/06* (2013.01)
*A61K 38/00* (2006.01)
(Continued)

(52) U.S. Cl.
CPC .......... *A61L 33/0011* (2013.01); *A61L 27/34* (2013.01); *A61L 31/10* (2013.01); *A61L 33/0047* (2013.01);
(Continued)

(58) Field of Classification Search
CPC .. A61L 2420/06; A61L 27/54; A61L 2300/42; A61L 2300/606; A61L 2300/608;
(Continued)

(56) References Cited

U.S. PATENT DOCUMENTS 5,132,108 A    7/1992  Narayanan
5,563,056 A *  10/1996 Swan ............... A61K 47/48007
                                                424/486
(Continued)

FOREIGN PATENT DOCUMENTS

WO    2009015420    2/2009

OTHER PUBLICATIONS

Bilek, et al., "Plasma-based ion implantation utilising a cathodic arc plasma", Surf Coat Technol., 156:136-42 (2002).
(Continued)

*Primary Examiner* — Ann Schillinger
(74) *Attorney, Agent, or Firm* — Pabst Patent Group LLP

(57) ABSTRACT

A plasma-activated coating (PAC) process covalently binds enzymes in their bioactive state, has low thrombogenicity and can be robustly applied to medical devices, resisting delamination when deployed in vivo. Applying this process to attachment of proteins such as enzymes that inhibit thrombosis and anticoagulants such as heparin or heparin fragments, one can produce medical devices and other materials for use in vascular applications having a number of benefits including covalent attachment, not requiring intermediate linkers or chemistry; substrate independent—works on polymers, metals, ceramics, 3D shapes like stents, valves, etc.; bioactivity is retained; surface may retain greater bioactivity over time in vivo; Simultaneously supports endothelialization; can be stored for long periods, following freeze drying, and retains effectiveness when rehydrated and; surface is able to bind many fibrinolytic enzymes such as streptokinase, urokinase, tPA, plasmin).

5 Claims, 4 Drawing Sheets

(51) Int. Cl.
| | |
|---|---|
| *A61L 33/00* | (2006.01) |
| *A61L 33/06* | (2006.01) |
| *B05D 7/00* | (2006.01) |
| *A61L 27/34* | (2006.01) |
| *A61L 31/10* | (2006.01) |
| *A61B 17/12* | (2006.01) |
| *A61B 17/00* | (2006.01) |
| *A61F 2/24* | (2006.01) |
| *A61F 2/82* | (2013.01) |
| *B05D 1/00* | (2006.01) |

(52) U.S. Cl.
CPC .............. *A61L 33/068* (2013.01); *B05D 7/58* (2013.01); *A61B 17/12109* (2013.01); *A61B 17/12122* (2013.01); *A61B 17/12177* (2013.01); *A61B 2017/00526* (2013.01); *A61B 2017/00575* (2013.01); *A61B 2017/00893* (2013.01); *A61F 2/24* (2013.01); *A61F 2/82* (2013.01); *A61F 2210/00* (2013.01); *A61L 2300/42* (2013.01); *A61L 2300/608* (2013.01); *B05D 1/62* (2013.01)

(58) Field of Classification Search
CPC .............. A61L 31/022; A61L 2300/252; A61L 2420/08; A61L 29/16; A61L 31/08; A61L 31/14; A61L 2300/204; A61L 2300/236; A61L 2300/25; A61L 2300/426
See application file for complete search history.

(56) References Cited

U.S. PATENT DOCUMENTS

| | | | |
|---|---|---|---|
| 8,808,365 B2 * | 8/2014 | Ng | .................. A61L 27/04 514/1.1 |
| 2003/0175408 A1 | 9/2003 | Timm | |

OTHER PUBLICATIONS

Chen, et al., "Surfaces having dual fibrinolytic and protein resistant properties by immobilization of lysine on polyurethane through a PEG spacer", J. Biomed. Mater. Res. A., 90:940-6 (2009).

Li, et al., "Mimicking the fibrinolytic system on material surfaces", Colloids Surf. B Biointerfaces, 86:1-6 (2011).

Marder, et al., "Thrombolysis with plasmin: implications for stroke treatment", Stroke J. Cereb, Circ., 41:845-9 (2010).

Nosworthy, et al., "The attachment of catalase and poly-l-lysine to plasma immersion ion implantation-treated polyethylene", Acta Biomater, 3:695-704 (2007).

Qu, et al., "A biologically active surface enzyme assembly that attenuates thrombus formation", Adv Func Mater., 21:4736-43 (2011).

Qu, et al., "Immobilization of actively thromboresistant assemblies on sterile blood-contacting surfaces", Adv. Healthcare Mat., 3:30-5 (2014).

Santos, et al., "Plasma-synthesised carbon-based coatings for cardiovascular applications", Biosurface Biotribology, 1(3):146-60 (2015).

Wang, et al., "A novel antithrombotic coronary stent: lysine-poly(HEMA)-modified cobalt-chromium stent with fibrinolytic activity", J. Biomater. Sci, Poly,. Ed., 24:684-95 (2013).

Waterhouse, et al., "The immobilization of recombinant human tropoelastin on metals using a plasma-activated coating to improve the biocompatibility of coronary stents", Biomaterials, 31:8332-40 (2010).

Waterhouse, et al., "In vivo biocompatibility of a plasma-activated, coronary stent coating", Biomaterials, 33:7984-92 (2012).

Wise, et al., "Immobilization of bioactive plasmin reduces the thrombogenicity of metal surfaces", Colloids Surf B Biointerfaces, 136:944-54 (2015).

Wu, et al., "Tissue plasminogen activator-containing polyurethane surfaces for fibrinolytic activity", Acta Biomater., 7:1993-8 (2011).

Yin, et al., "Covalent immobilisation of tropoelastin on a plasma deposited interface for enhancement of endothelialisation on metal surfaces", Biomaterials, 30:1675-81 (2009a).

Yin, et al., "Acetylene plasma polymerized surfaces for covalent immobilization of dense bioactive protein monolayers", Surf. Coat. Technol., 203:1310-6 (2009a).

* cited by examiner

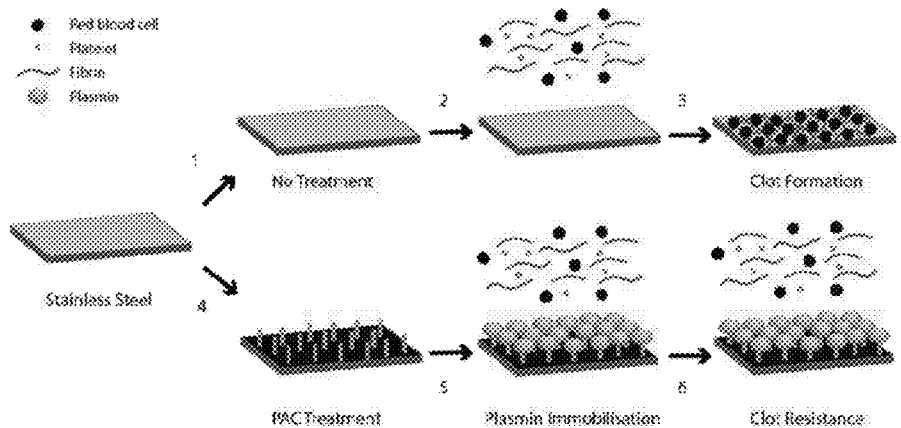
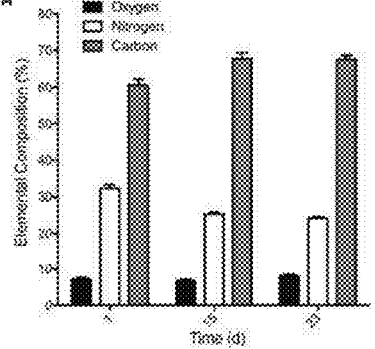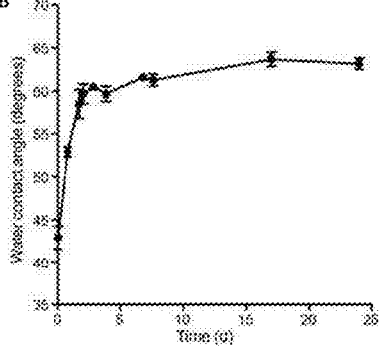
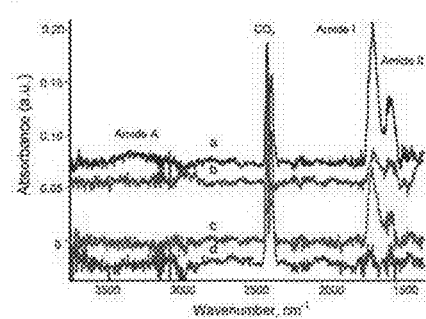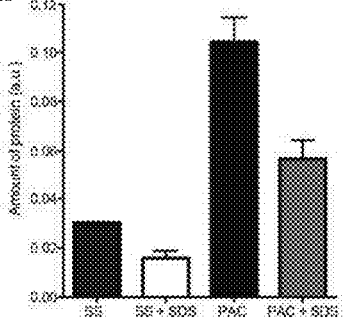
Figure 1
Figure 2A  Figure 2B
Figure 2C  Figure 2D

MEDICAL DEVICES WITH REDUCED THROMBOGENICITY

CROSS REFERENCE TO RELATED APPLICATION

This application claims benefit of and priority to U.S. Provisional Application No. 62/049,879, filed Sep. 12, 2014, all of which is incorporated by reference in its entirety.

FIELD OF THE INVENTION

The present disclosure relates generally to biomaterials with improved blood compatibility, made by immobilizing proteins such as blood enzymes for reduced surface thrombogenicity using plasma activation of the substrate for attachment.

BACKGROUND OF THE INVENTION

Despite the increasing incidence of cardiovascular disease, there are few effective biomaterials currently available for clinical vascular applications. Currently available synthetic biomaterials such as polyethylene terephthalate have a range of vascular applications including endovascular grafting, heart valve replacement, vascular/myocardial patches and vascular closure devices, but perform poorly as vascular surgical conduits.

An increasing number of implantable devices used in cardiovascular repair, including heart valves and endovascular stents, are made using metal alloys (Singh et al., *J. Mat. Sci. Mat. Med.*, 18:725 (2007)). Metallic surfaces are inherently thrombogenic, a property that is currently masked with profound pharmacological platelet suppression. Following deployment of a stent, the low rates (1-2%) of early thrombosis are maintained only with adherence to dual antiplatelet therapy (DART) with aspirin and a thienopyridine (Urban et al., *Lancet*, 369:619 (2007)). In the era of drug-eluting stents (DES), the appropriate duration of DAPT remains unclear, but it is increasingly recognized to be dependent on the stent platform. The latest clinical data demonstrate that second generation zotarolimus-eluting DES continue to carry an ongoing risk of thrombosis of up to 0.6% per year, increasing dramatically to 3.6% if DAPT is discontinued within the first month. Confounding this issue, DAPT carries an inherent risk of bleeding, significantly increasing if therapy is continued for 12 months or longer (Valgimigli et al, *Circulation*, 125:2015 (2012)). A stent platform with enhanced hemocompatibility would provide a clear benefit.

The removal of fibrin and the breakdown of blood clots, termed fibrinoloysis, centrally involves plasminogen. A variety of activating factors, including tissue plasminogen activator (tPA), cleave plasminogen to its active form, plasmin (Marder et al., *Stroke J. Cereb. Circ.*, 41:S45 (2010)). Plasmin is a 90 kDa, two-chain proteolytic enzyme, capable of degrading multiple proteins in both the plasma and extracellular space, but in particular fibrin. For materials applications, adaptation of this pathway to generate clot lysing surfaces has generated much interest (Li et al., *Colloids Surf. B Biointerfaces*, 86:1 (2011)). One approach has been to expose lysine-rich surfaces to plasma, preferentially sequestering plasminogen for further activation. In vitro, this method has shown clot lysis on both polyurethane and cobalt-chromium substrates (Chen et al., *J. Biomed. Mater. Res. A.*, 90:940 (2009); Wang et al., *J. Biomater. Sci. Poly., Ed.*, 24:684 (2013)). Alternatively, direct immobilization of endogenous regulators of thrombus formation, such as thrombomodulin or tPA onto biomaterial surfaces has shown promise, though necessitating a series of chemical intermediates attached to a polyurethane interface for attachment (Qu et al., *Adv. Healthcare Mat.*, 3:30 (201.4); Wu et al., *Acta Biomater.*, 7:1993 (2011)).

This work highlights important challenges in the adaptation of fibrinolytic agents to enhance biomaterial hemocompatibility, including the need for complex linker chemistry schemes for robust attachment and the long-term retention of biologically active substrates. Adaptation to inert metal platforms with varied three-dimensional geometries such as stents further accentuates these difficulties.

It is an object of the present invention to provide materials which are suitable for vascular application that are biocompatible and not thrombogenic having very low thrombogenicity and a method for safely and securely attaching them to medical substrates without altering or decreasing activity.

SUMMARY OF THE INVENTION

A plasma-activated coating (PAC) process covalently binds enzymes in their bioactive state, has low thrombogenicity and can be robustly applied to medical devices, resisting delamination when deployed in vivo. Applying this process to attachment of proteins such as enzymes that inhibit thrombosis and anticoagulants such as heparin or heparin fragments, one can produce medical devices and other materials for use in vascular applications having a number of benefits including:

1) covalent attachment, does not require intermediate linkers or chemistry—simple incubation with PAC only;
2) substrate independent—works on polymers, metals, ceramics, 3D shapes like stents, valves, etc.;
3) bioactivity is retained;
4) Surface may retain greater bioactivity over time in vivo;
5) Simultaneously supports endothelialisatio;
6) Can be stored for long periods, following freeze drying, and retains effectiveness when rehydrated and;
7) Surface is able to bind many fibrinolytic enzymes such as streptokinase, urokinase, tPA, plasmin).

The plasma process contains nitrogen and acetylene, and importantly deposits an activated carbon-based film on the substrate that facilities covalent attachment of biomolecules. This is in contrast to other methods that rely on release of active in combination with inert materials.

Preferred enzymes include streptokinase, urokinase, tissue plasminogen activator (tPA), and plasmin. Other materials such as heparin and heparin fragment can also be immobilized on metal or polymeric substrates.

Components of endovascular steins, heart valves and cardiac rhythm devices are made using metal alloys. In these blood contacting applications, all metallic devices have high rates of thrombosis which are managed clinically only with profound platelet suppression. In one preferred embodiment, the engineered materials form a stent which has reduced thrombogenicity and increased endothelialization due to a PAC process that enables the immobilization of a non-thrombogenic protein to the stent. The technology is useful for many other implants and devices, including heart valves, vascular meshes, heart and lung bypass machines, implantable pumps, and implantable valves.

BRIEF DESCRIPTION OF TUE DRAWINGS

FIG. 1 is a schematic showing the steps or stages of plasmin immobilization. In the absence of modification (Step 1), stainless steel recruits platelets and red blood cells, and activates fibrin (Step 2), leading to clot formation (Step 3). Following surface activation with the PAC process (Step 4), plasmin can be covalently retained (Step 5) and it can prevent the formation of fibrin networks, resisting clot formation (Step 6).

FIG. 2A is a graph showing the elemental composition of PAC over time as measured by X-Ray Photoelectron Spectroscopy (XPS). Relative oxygen content remains stable, while marginal increases in the carbon are offset by reduced nitrogen.

FIG. 2B is a graph showing that the water contact angle of PAC stabilizes at approximately 62°, indicating a mildly hydrophobic interface.

FIG. 2C is a graph showing Fourier Transform Infrared Spectroscopy (FUR) spectra of plasmin coated on stainless steel (SS) and PAC, before and after SDS washing in each case.

FIG. 2D is a graph showing that quantification of amide peaks infers the covalent retention of plasmin on PAC, in contrast to complete removal on stainless steel.

Figure 3A:
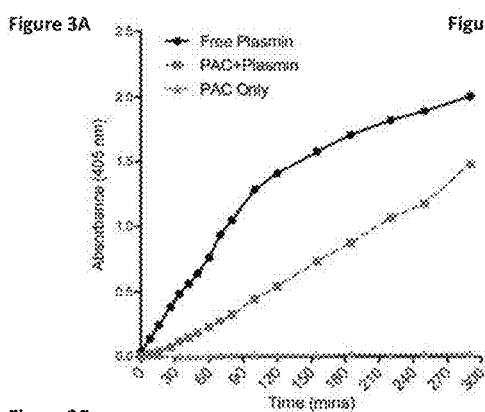

FIG. 3A is a graph of a D-Val-Leu-Lys-p-Nitroanilide (VALY) activity assay, showing increasing cleavage of the substrate over time for free plasmin in solution. When bound to PAC, plasmin remained active, also showing increased absorbance over time. No signal was observed for PAC alone.

Figure 3B:
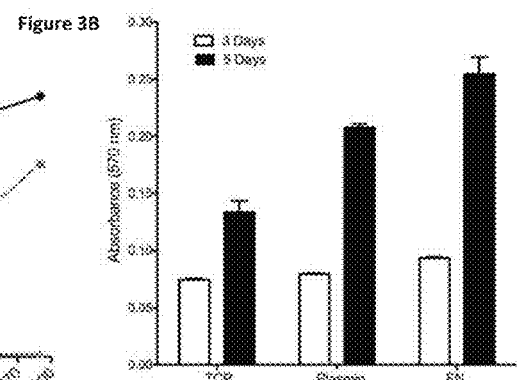

FIG. 3B is a graph showing endothelial cell proliferation on uncoated tissue culture plastic (TCP), compared to TCP coated with plasmin or fibronectin (FN). Plasmin coated surfaces support an increase in endothelial cell numbers from 3 to 5 days, greater than TCP alone.

Figure 3C:
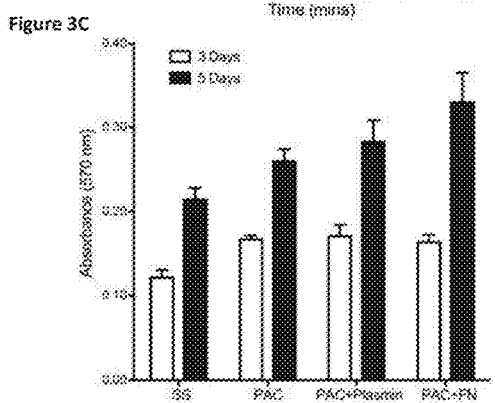

FIG. 3C is a graph showing that when immobilized on PAC, plasmin supported endothelialization up to 5 days, comparable to FN.

Figure 4:
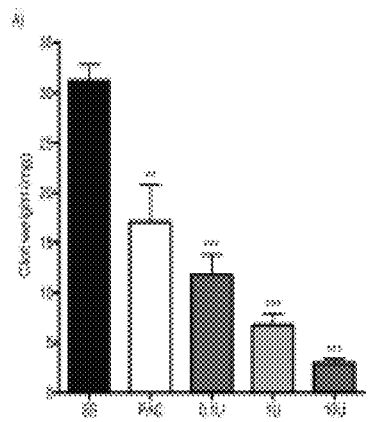

FIG. 4 is a graph demonstrating the relative thrombogenicity of SS, PAC alone, and plasmin covalently pound to PAC was studied using a whole blood adhesion assay. Increasing concentrations of plasmin, 0.1 U, 1.0 U, and 10 U, immobilized on PAC demonstrated a dramatic reduction of thrombus weight in a dose dependent manner, compared to SS controls. PAC alone reduced thrombus weight 45.4±9.1%, but further reductions were observed for 0.1 U (62.3±6.4%), 1 U (78.3±6.4%) and 10 U (90.5±1.3%) plasmin, relative to SS ($p<0.001$).

Figure 5A:
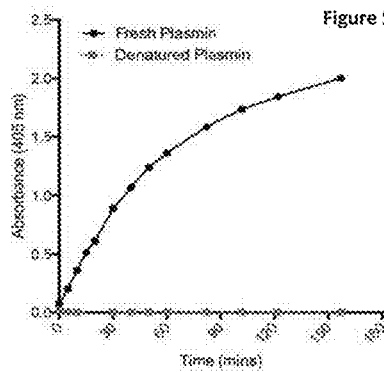
Figure 5B:
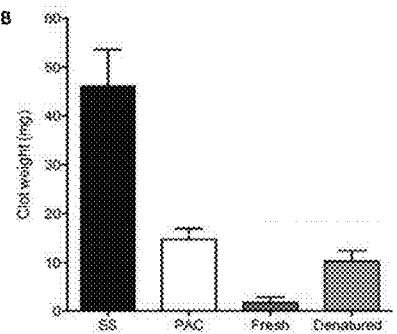
Figure 5C:
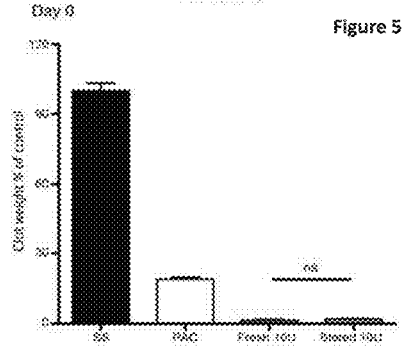

FIGS. 5A-5D are graphs directly assessing the contribution of surface bound plasmin, following denaturation of the enzyme prior to incubation with PAC. Following repeat freeze-thaw cycles, plasmin was confirmed to be inactive using the VAIN conversion described above (FIG. 5A). Denatured plasmin bound surfaces continued to show superiority to SS, but were statistically equivalent to PAC only surfaces and has significantly higher clot weights than fresh plasmin on PAC (FIG. 5B). Considering the potential to store plasmin coated PAC surfaces, samples were freeze dried prior to rehydration and re-testing with whole blood. Immediately following freeze drying (FIG. 5C) and up to 14 weeks later (FIG. 5D), clot weights of freshly prepared and stored plasmin on PAC were equivalent.

Figure 5D:
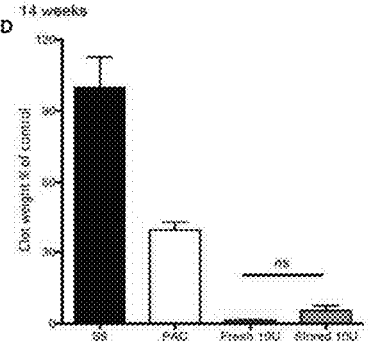

Plasmin was denatured by autoclaving prior to PAC immobilization, leading to a complete loss of VAIN assay activity (FIG. 5A). Denatured plasmin was unable to reduce thrombus formation beyond the effect of PAC alone, and clot weight was significantly greater than that resulting from freshly prepared plasmin (FIG. 5B). The blood compatibility of 10 U plasmin was retained after freeze-drying and immediate rehydration (FIG. 5C); as well as after 14 weeks of storage at 4° C. prior to rehydration (FIG. 5D).

Figure 6A:
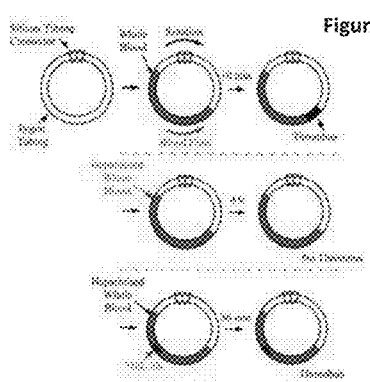
Figure 6B:
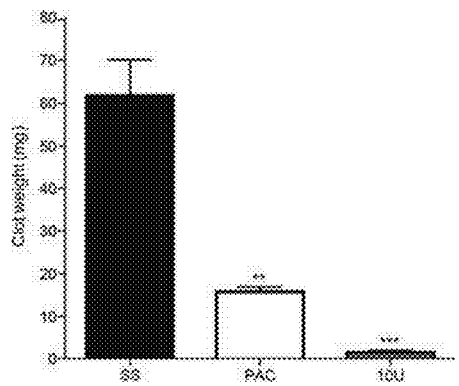
Figure 6C:
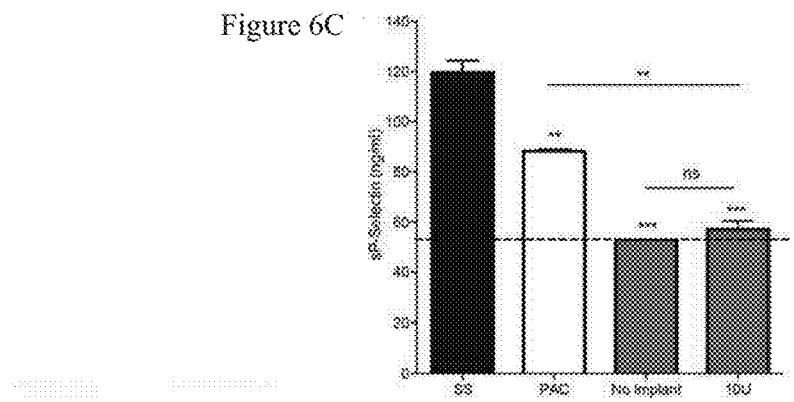

FIG. 6A illustrates the steps in a modified Chandler Loop Assay, which show that under flow conditions, stainless steel samples led to substantial thrombus formation. FIG. 6B is a graph showing that the 10 U plasmin surface reduced clot weight by 97.97±1.3%, relative to stainless steel and PAC alone ($p<0.001$). Under flow conditions in a modified Chandler loop (FIG. 6A), stainless steel ("ss") samples generated substantial thrombus formation (61.8±8.3 mg, FIG. 6B). In contrast, the thrombogenicity of PAC alone was reduced significantly to 15.8±1.1 mg ($p<0.001$), while immobilization of 10 U plasmin on PAC further reduced clot weight to 1.4±0.4 mg ($p<0.001$), a 97.7±1.3% reduction relative to SS controls. FIG. 6C is a graph of sP-Selectin (ng/ml) for ss, PAC, No implant, and 10 U plasmin immobilized on PAC.

DETAILED DESCRIPTION OF THE INVENTION

I. Definitions

The term "assay" as used herein refers to the analytic procedure for qualitatively assessing or quantitatively measuring the presence or amount or the functional activity of a target entity (the analyte).

The term "Chandler Loop Assay" as used herein refers to a system of rotating tubes that simulates the circulation of blood. This assay is suitable for testing the hemocompatibility of medical devices placed into the blood stream.

The term "coagulation" or "blood clotting" as used herein refers to the process by which blood changes from a liquid to a gel. It potentially results in hemostasis, the cessation of blood loss from a damaged vessel, followed by repair.

The term "coating" or "coated" as used herein refers to the functional layer of material that is applied to the surface of an object, usually referred to as the substrate.

The term "covalent bonding" as used herein refers to the chemical bond that is formed as a result of the stable balance of attractive and repulsive forces between atoms when they share electrons.

The term "endothelial cells" as used herein refers to the cells that line the blood vessels.

The term "enzyme" as used herein refers to a biological catalyst that facilitates a metabolic process.

The term "fibrin" as used herein refers to a fibrous, non-globular protein involved in the clotting of blood. It is formed by the action of the protease thrombin on fibrinogen, which causes the latter to polymerize. The polymerized fibrin together with platelets forms a hemostatic plug or clot over the wound site.

The term "fibrinolysis" as used herein refers to the degradation of fibrin.

The term "fibrinolytic" as used herein refers to the ability of a substance to degrade fibrin and hence prevent blood clots from growing and becoming problematic.

The term "freeze-dried" or "lyophilized" as used herein refers to materials that are dehydrated for the purpose of preservation.

The term "hemocompatible" refers to a set of properties that allow contact with flowing blood without causing adverse reactions such as thrombosis, hemolysis, complement activation, or inflammation.

The term "immobilization" as used herein refers to the attachment of a substance to an inert, insoluble material, allowing for increased resistance to changes in conditions such as pi or temperature. In particular, it allows enzymes to be held in place throughout a reaction, thus facilitating their reuse.

The term "mediator" as used herein refers to an agent that mediates a physical, chemical, or biological process, such as a coating that facilitates the immobilization of enzymes to a substrate.

The term "non-thrombogenic" as used herein refers to the tendency of a material in contact with the blood to prevent the formation of a thrombus, or clot.

The term "plasma-activated coating" or "PAC" as used herein refers to a process of immobilizing plasmin on stainless steel substrates using a plasma-activated coating mediator to create a surface that substantially attenuates thrombus formation.

The term "plasmin" as used herein refers to the enzyme present in blood that degrades many blood plasma proteins, including fibrin clots.

The term "plasminogen" as used herein refers to the blood circulating glycoprotein which is the precursor of plasmin.

The term "platelets" or "thrombocytes" as used herein refers to blood cells whose function is to stop bleeding. Platelets have no nucleus, they are fragments of cytoplasm which are derived from the megakaryocytes of the bone marrow, and then enter the circulation.

The term "reduced" as used herein refers to having been made smaller or less in amount, degree, or size.

The term "stent" as used herein refers to a mesh tube that is inserted into a natural passage or conduit in the body to prevent or counteract a disease-induced, localized flow constriction.

The term "streptokinase" as used herein refers to the enzyme secreted by several species of streptococci that can bind and activate human plasminogen.

The term "substrate" as used herein refers to the material that underlies the mediator and non-thrombogenic protein.

The term "thrombin" as used herein refers to the serine protease that converts soluble fibrinogen into insoluble strands of fibrin, and that catalyzes many other coagulation-related reactions.

The term "thrombogenicity" as used herein refers to the tendency of a material in contact with the blood to produce a thrombus, or clot.

The term "thrombosis" as used herein refers to the formation of a blood clot inside a blood vessel that obstructs the flow of blood through the circulatory system.

The term "thrombus" or "blood clot" as used herein refers to a solid or semi-solid mass formed from the constituents of blood within the vascular system that is the product of blood coagulation. There are two components to a thrombus, aggregated platelets that form a platelet plug, and a mesh of cross-linked fibrin protein.

The term "tissue plasminogen activator" or "tPA" as used herein refers to a protein involved in the breakdown of blood clots. It is a serine protease found on endothelial cells. As an enzyme, it catalyzes the conversion of plasminogen to plasmin, the major enzyme responsible for clot breakdown.

The term "urokinase" as used herein refers to the serine protease that is present in the bloodstream and acts on plasminogen.

The term "valve" as used herein refers to a device that controls the passage of fluid through a pipe or duct, allowing movement in one direction only.

The term "VAIN" as used herein refers to the plasmin substrate D-Val-Leu-Lys-p-Nitroanilide.

The term "VALY activity assay" as used herein refers to an assay that measures the cleavage of VALY by plasmin into p-Nitroanilide and D-Val-Leu-Lys.

The term "zymogen" as used herein refers to an inactive enzyme precursor that requires biochemical change to become an active enzyme.

II. Compositions

It has been discovered that plasma polymerization of a substrate can greatly enhance biocompatibility, which is further enhanced by coupling of enzymes and other anti-thrombotics such as heparin that inhibit clotting and platelet activation. These are collectively referred to herein as "anti-thrombotics". The anti-thrombotic coating is robust enough to withstand deployment and blood flow and presents the anti-thrombotic in a biologically active conformation, thereby decreasing thrombogenicity.

A. Substrate Processed Plasma Polymerisation

The enzyme is covalently bound to metal substrates via a polymer intermediary such as acetlyene (ethylene). The acetylene layer is blended with the metal surface using plasma polymerisation, converting the inert metal surface into a reactive polymer surface. The composition of the polymer layer can be widely varied and conditions for optimal anti-thrombotic binding varied. Similar results can be achieved using other carbon chains (such as hexane) or different plasma conditions.

FIG. 1 is a schematic showing the steps or stages of plasmin immobilization. In the absence of modification (Step 1), stainless steel recruits platelets and red blood cells, and activates fibrin (Step 2), leading to clot formation (Step 3). Following surface activation with the PAC process (Step 4), plasmin can be covalently retained (Step 5) and it can prevent the formation of fibrin networks, resisting clot formation (Step 6).

Given the current problems with regards to late stent thrombosis in drug eluting stents, many groups are exploring the use of biodegradable coatings for drug release. In such instances, a biodegradable drug release coating may be applied over a biocompatible coating such as enzyme covalently bound by plasma polymerization. This would allow local elution of a drug, leaving behind a stent with a biocompatible coating.

Stents can also be manufactured from degradable materials as alternatives to permanent metallic scaffolds. These bioresorbable stents have commonly been manufacted from polymers such as poly-lactic acid and polyglycolic acid, which remain in the body for 6-24 months (Zilberman and Eberhard, *Ann. Rev. Biomed. Eng.*, 8:153-180 (2006)). Bioresorbable stents can also be made from metal alloys such as magnesium. These are completely resorbed within 2 months and have shown promising clinical outcomes (Erbel, Di Mario, et al., *Lancet*, 369:1869-75 (2007)). Plasma polymerisation and/or coating with enzyme is also relevant to the improvement of the short term biocompatibility of these temporary scaffolds and could easily be adapted for their modification.

Materials which can be plasma polymerized include metals, polymers, carbon, and ceramic. The anti-thrombotic, can be applied to, crosslinked with, tethered to, blended with, or laminated as part of, one or more materials to form a surface, component, or device. In the preferred embodiment, a graded polymer such as acetylene layer is deposited on the surface of a metal, such that the initial deposition is metal, with increasing polymer, finishing with 100% polymer. The effect of this graded layer is that there is no defined metal/polymer interface and no resultant peeling off of the coating. The polymer layer is chemically activated using treatment with gas plasma, pre-disposing it to form covalent bonds with anti-thrombotics. Immersion of the plasma polymerised surface in a anti-thrombotic solution is sufficient for covalent attachment, with no separate cross-linking agent required. Importantly, bioactivity is retained.

Typical metals include stainless steel and titanium. In one embodiment, the material is or includes one or more biodegradable or non-biodegradable synthetic polymers such as polylactides, polyglycolic acids, polycaprolactones, polycaprolactams, polyhexamethylene adipamide, polycarbonates, polyamides, polyanhydrides, polyamino acids, polyesters, polyacetals, polycyanoacrylates, polyvinyl alcohols, polyvinyl chlorides, polyethylenes, polyurethanes, polypropylenes, polyacrylates, polystyrenes, polyvinyl oxides, polyvinyl fluorides, poly(vinyl imidazoles), polyethylene oxides, polytetrafluoroethylenes, silicone polymers and copolymers and combinations thereof. In another embodiment, the material is or includes one or more natural materials such as a protein, sugar or polysaccharide, or combination thereof. Representative examples include collagen, preferably type 1 and/or type 3, fibrin, gelatin, vitronectin, fibronectin, hyaluronic acid, glycosaminoglycans, their derivatives and mixtures thereof. Preferred glycosaminoglycans include chondroitin sulfate, dermatan sulfate, keratan sulfate, heparan sulfate, heparin and hyaluronan.

The application will determine the selection and design of the mechanical properties. The material can be applied as a part of a variety of clinical vascular applications including a vascular conduit, a stent, a stent-graft, a surgically or percutaneously implantable heart valve, a vascutarlseptal occlusion device, avascular closure device, endovascular implant, stent graft, graft, pacemaker lead vascular occluder, left atrial appendage occlusion device, endovascular valve, vascular closure devices including atrial septal and patent foramen ovale closure, or vena caval filters, or as a surface coating for a vascular device/application.

The protein can also be used to form coatings on materials such as microchips, which may be formed of a material such as a silicon chip, which may be used as sensors, electrodes, or for drug delivery, or a device such as an implantable pump.

Other useful materials are matrices for tissue engineering and/or drug delivery, bone implants and prosthetics including pins, rivets, screws and rods, as well as artificial knees and other joints, especially at the surfaces where the metal, ceramic or bone interfaces with the host tissue. In the majority of these cases, the critical role of the enzyme is to increase the biocompatihility of the implant or matrix, promoting cell attachment or diminishing the formation of scar tissue, abnormal proliferation of cells (i.e., restenosis or scarring), and integration of the implant into the host.

B. Anti-Thrombotic Agents

Preferred enzymes include streptokinase, urokinase, tissue plasminogen activator (tPA) including alteplase, reteplase, tenecteplase and desmoteplase, and plasmin. Other anti-thronogenic proteins such as direct thrombin inhibitors (e.g. bivalirudin etc.) and anti-platelet agents can also or alternatively be immobilized on the substrates. Other materials such as heparin and heparin fragment can also be immobilized on metal or polymeric substrates.

These are all commercially available.

III. Methods of Manufacture of Materials and Devices

A plasma-activated coating (PAC) process covalently binds biomolecules in their bioactive state, has low thrombogenicity and can be robustly applied to medical devices, resisting delamination when deployed in vivo (Yin et al., *Biomaterials*, 30:1675 (2009); Waterhouse et al., *Biomaterials*, 31:8332 (2010); Waterhouse et al., *Biomaterials*, 33:7984 (2012)).

The substrate material is modified to create reactive surface groups which facilitate covalent interaction. In the case of inert polymeric materials like ePTFE, the surface requires activation. Both 'classical' plasma processes (Bilek et al. (2004) In *Smart Materials III*, Vol. 5648 (Ed, Wilson, A. R.) SPIE, pp. 62-67) and higher energy plasma immersion ion implantation (Bilek, et al. *Surface and Coatings Technology*, 156:136-142 (2002)) (PIII) can be used.

In a preferred embodiment, the enzyme is covalently tethered to the polymer when a solution of the protein is incubated with the activated surface. PIII has recently been shown to increase the functional lifetime of attached proteins and may be preferred (Nosworthy, et al. *Acta Biomater,* 3:695-704 (2007)).

Metallic substrates can be also be functionalized by applying a modified plasma process to the substrate while it is immersed in a carbon containing plasma or in a vapor of the monomer used to deposit the plasma polymer layer or by codeposition of a graded substrate/polymer layer which terminates in the polymer (Yin, et al., *Surf. Coat. Technol.*, 203:1310-1316 (2009)). A range of short chain carbon-based polymers including hexane and acetylene can be used to form the basis of the plasma polymer layer. The plasma chamber also contains a background carrier gas, examples of which include oxygen, hydrogen, argon, nitrogen and combinations thereof. This plasma mixture is essential to efficacy.

In a preferred embodiment acetylene is injected into the plasma chamber and activated together with a combination of nitrogen and argon background gas, subsequently condensing to form polymerized surfaces. This technique can be used to bind enzyme to a range of metals including stainless steel, as demonstrated by Yin, et al., *Biomaterials*, 30:1675-1681 (2009).

The present invention will be further understood by reference to the following non-limiting examples.

EXAMPLES

Example 1. Covalent Immobilization of Plasmin to PAC

Materials and Methods

Reagents: All reagents were purchased from Sigma-Aldrich, St Louis and used without further purification unless otherwise noted. Human umbilical vein endothelial cells (HUVECs) were harvested enzymatically from umbilical cords. Endothelial cells from passages 2-4 were used.

Sample Preparation:

The substrates were 316L, stainless steel foil (SS) 25 µm thick (Brown Metals), or 3.0×10 mm 316LVM stainless steel stents (Laserage, Calif., USA). Plasma-activated coating on 316L stainless steel (PAC) surfaces were generated from acetylene in, argon mixed with nitrogen. Stainless steel stents were imaged with a Zeiss EVO 50 scanning electron microscope. Samples were incubated with increasing concentrations of plasmin (0.1, 1.0 and 10 µg) in PBS at 37° C. overnight and washed in PBS prior to use.

Surface Characterization:

The contact angle between PAC and de-ionized water was measured using a Kruss contact angle analyzer DS10 employing the sessile drop method. X-ray photoelectron spectroscopy (XPS, Specs-XPS, mode XP-50 High Performance Twin Anode with Focus 500 Ellipsoidal Crystal Monochromator and PROMOS 150 MCD-9 analyser) was utilized to provide data on the elemental composition of PAC variants over time. CASA XPS was used to calculate areas of elemental peaks with the concentration of each element expressed as an atomic percentage.

Results

As shown in FIG. 2A, the relative percentage of nitrogen in the surface decreased from 32.3±1.0% on day 1, to 24.2±0.5% on day 23. This corresponded to a small increase in oxygen from 7.1±0.5% up to 8.2±0.3% and in the relative carbon content from 60.6±1.7% to 67.6±1.1% from day 1 to 23, respectively. The starting water contact angle of the PAC was 42.9±2.4° 30 minutes after treatment, increasing to 52.9±1.0° after 2 hours (FIG. 2B). Surface chemistry appeared to have stabilized by day 7, when the water contact angle was observed to be 61.6±0.4°. Only minor changes were observed from this time, out to 24 days.

Spectra of PAC and SS surfaces after incubation with plasmin contained characteristic peaks associated with the internal protein vibrations and confirmed the presence of a cross-linked polymeric layer containing predominantly carbon and nitrogen, with hydrogen and oxygen terminations (FIG. 2C). Bond vibrations attributed to both saturated and unsaturated C—C and C—N bonds are Observed. C—H, O—H, and N—H absorptions indicate that hydrogen terminations are present and that the surface has been oxidized by exposure to atmosphere. The relative intensities of characteristic amide A, I, and II FTIR peaks for plasmin were compared before and after washing with detergent (FIG. 2I)). After detergent washing, surfaces displayed only covalently attached plasmin, with retention of 54.2±3.8% of originally bound plasmin on PAC, but complete removal from stainless steel.

Example 2. Covalently Bound Plasmin Retains Bioactivity

Materials and Methods
Covalent Attachment:

Samples were washed with water to remove salt and dried prior to accumulation of spectra using a Digilab FTS7000 FTIR spectrometer fitted with an attenuated total reflection (ATR) accessory with a trapezium germanium crystal at incidence angle of 45°. To obtain sufficient signal/noise ratio and resolution of spectral bands, 500 scans with a resolution of 1 cm$^{-1}$ were taken. Difference spectra were used to detect changes associated with the presence of plasmin, and analysis carried out. Unbound protein was removed by aspiration and the surfaces were washed with PBS. Non-covalently bound protein was removed by SDS-washing. Samples were treated with 5% (w/v) SDS for 1 h at 80° C. Following the SDS treatment, samples were washed with PBS and distilled water.

Bioactivity Assay:

The enzymatic activity of plasmin was monitored using a commercially available kit. One unit of activity is defined as the production of one micromole of p-Nitroartilide from D-Val-Leu-Lys-p-Nitroanilide (VALY) at pH 7.5 at 37° C. Activity was monitored over time, up to 210 mins, and compared free plasmin in solution to plasmin immobilized on PAC and PAC alone as a negative control.

Results

Measuring the color change that occurs as VALY is converted to p-Nitroanilide at 405 nm was used to monitor the enzymatic activity of plasmin. Both fresh plasmin solution and plasmin immobilized on PAC were able to convert the substrate, showing an increased absorbance over the time course, up to 290 minutes (FIG. 3A). PAC alone did not produce p-Nitroanilide.

Example 3. Effect on Cell Attachment and Proliferation

Materials and Methods
Endothelial Cell Interactions:

For proliferation assays, HUVECs (20,000 cells/mL) were plated in 24-well plates for 3 and 5 days. Attachment and proliferation of cells to and on plasmin-coated wells was analyzed in comparison to tissue culture plastic alone and to wells coated with fibronectin (10 µg/well). Cells were quantified at 3 and 5 days post-seeding using the MTT (3-[4,5-dimethylthiazol-2-yl]-2,5 diphenyl tetrazolium bromide) assay according to manufacturer's instructions. Dimethyl sulfoxide (DMSO) was used to dissolve insoluble formazan crystals, and the absorbance at 540 nm was measured using a spectrophotometer (Biorad).

Results

After 3 days of incubation, cell numbers on TCP, plasmin and fibronectin (FN) were not significantly different (FIG. 3B). At day 5, cell proliferation on plasmin was 56.40±3.2% higher than TCP alone (p<0.001), but remained statically less than then FN positive control, which was a further 22.12±1.8% higher than plasmin (p<0.01). When immobilized on PAC, there was again no significant difference between the conditions on day 3 (FIG. 3C). By day 5, PAC and PAC+plasmin showed a 20.47±1.6% and 31.16±2.4% increase over stainless steel (SS) respectively, though this did not reach statistical significance. PAC+FN increased HUVEC proliferation 53.49±2.8% (p<0.01) over stainless steel, but only 17.02±1.2% more than PAC+plasmin (p=ns).

Example 4. Thrombogenicity In Vitro

Materials and Methods
Thrombogenicity Assessment:

Whole blood was obtained from healthy, non-smoker, male volunteers with informed consent in accordance with the Declaration of Helsinki, who had not taken aspirin two weeks prior to donation. Approval for this work was granted by The University of Sydney, Human Research Ethics Committee (protocol 05-2009/11668). Experiments were conducted at least three times with different donors' blood. Samples of SS, PAC or PAC+plasmin were incubated with heparinized whole blood (0.3 U/ml) for 30 min at 37° C. whilst rocking. Concentrations of plasmin increased from 0.1-10 U were used initially to determine an optimal coating density. Thrombogenicity under flow conditions was investigated using a modified Chandler loop. Briefly, samples were balloon expanded into 28 cm lengths of Tygon S-50-Ht tubing (SDR, Australia), connected into loops using 1 cm silicone connectors and filled with heparinized whole blood (0.5 U/ml, 2.5 ml). The loops were rotated at 34 rpm at 37° C. for 60 min. The thrombus and steel from each loop was removed for imaging and weighing. The blood from each loop was combined with 10% (v/v) acid citrate dextrose (ACD) and centrifuged at 1000 rpm for 15 min to obtain serum. Soluble P-selectin was detected via an ELISA (R&D Systems, USA). For stent evaluation, 0.3 U/ml heparin, 90 mins, was evaluated.

Results

The relative thrombogenicity of stainless steel, PAC alone, and plasmin covalently bound to PAC was studied using a whole blood adhesion assay (FIG. 4). Increasing concentrations of plasmin, 0.1 U, 1.0 U, and 10 U, immobilized on PAC demonstrated a dramatic reduction of thrombus weight in a dose-dependent manner, compared to stainless steel controls. PAC alone reduced thrombus weight by 45.4±9.1%, but further reductions were observed for 0.1 U (62.3±6.4%), 1 U (78.3±6.4%) and 10 U (90.5±1.3%) plasmin, relative to stainless steel (p<0.001). The reductions in thrombus weight are also demonstrated in representative images of the samples. Surface fibrinolysis was also demonstrated by incubation with whole blood containing fluorescently labeled fibrinogen. A complete interconnected fibrin network was observed on stainless steel after 30 minutes, while on PAC only this network was also present but notably less dense. On plasmin coated PAC only the rudiments of interconnected fibrin were observed.

To more directly assess the contribution of surface-bound plasmin, the enzyme was denatured prior to incubation with PAC. Following repeated freeze-thaw cycles, plasmin was confirmed to be inactive using the VALY conversion described above (FIG. 5A). Denatured plasmin-bound surfaces continued to show superiority to stainless steel, but were statistically equivalent to PAC only surfaces and had significantly higher clot weights than fresh plasmin on PAC (FIG. 5B).

Considering the potential to store plasmin coated PAC surfaces, samples were freeze-dried prior to rehydration and re-tested with whole blood. Immediately following freeze-drying (FIG. 5C) and up to 14 weeks later (FIG. 5D), clot weights of freshly prepared and stored plasmin on PAC were equivalent.

Under flow conditions in a modified Chandler loop (FIG. 6A), stainless steel samples generated substantial thrombus formation (61.8±8.3 mg) (FIG. 6B). In contrast, the thrombogenicity of PAC alone was reduced significantly to 15.8±1.1 mg (p<0.001), while immobilization of 10 U plasmin on PAC further reduced clot weight to 1.4±0.4 mg (p<0.001), a 97.7±1.3% reduction relative to stainless steel controls. These differences are well demonstrated in the representative images, which show a clear contrast between the clotted stainless steel samples, and the 10 U plasmin samples, which are largely thrombus free.

This striking thrombus reduction was driven by a significant decrease in the amount of sP-Selectin detected in the samples (FIG. 6D). Stainless steel controls, activating platelets generated 119.7±4.8 ng/ml of sP-Selectin, reduced to 88.1±0.9 ng/ml in the presence of PAC only. Addition of plasmin to PAC resulted in a further reduction to 57.16±3.5 ng/ml, significantly lower than both stainless steel (p<0.001) and PAC alone (p<0.01), and not significantly different from the no implant control which represents the baseline level of activation in this assay.

Stainless steel stents (3 mm×10 mm, 316 LVM) were laser cut and electropolished to remove any surface contaminants. PAC treated stents were macroscopically darker than untreated stainless steel stents. Under scanning electron microscopy (50× magnification), PAC coated stents had a smooth, contiguous appearance, free from cracking or delamination. The blood compatibility of stainless steel, PAC only and PAC+plasmin steins was demonstrated by incubation with whole blood containing fluorescently labeled fibrinogen in a Chandler Loop. After 15 minutes, only faint fluorescence was observed for all conditions. In contrast, after 30 minutes, significant fibrin deposition was observed for stainless steel, while little was seen on PAC+ plasmin. Fibrin fluorescence on PAC only was intermediate between these two conditions.

We claim:

1. A vascular medical device comprising a surface consisting of
   a plasma polymerized biocompatible coating of polyhexane or polyacetylene with surface reactive groups having nitrogen incorporated therein on a metallic, ceramic, carbon or polymeric substrate of the device which contacts blood,
   having plasmin covalently bound to the surface reactive groups.

2. The device of claim 1 wherein the device is a stent.

3. The device of claim 1 wherein the device is a heart valve, prosthesis, implanted valve, implanted pump, heart-lung bypass machine components in contact with blood, endovascular implant, stent graft, graft, pacemaker lead vascular occluder, left atrial appendage occlusion device, endovascular valve, vascular closure devices including atrial septal and patent foramen ovale closure, or vena caval filters.

4. The device of claim 1 wherein the device can be freeze-dried.

5. A method for manufacturing a vascular medical device as described in claim 1, comprising
   (a) plasma polymerizing polyhexane or polyacetylene in nitrogen or a mixture of argon and nitrogen to form a coating of polyhexane or polyacetylene with surface reactive groups having nitrogen incorporated therein on a polymeric, metallic, ceramic or carbon surface or component of the device which contacts blood, and
   (b) covalently binding plasmin to the surface reactive groups.

* * * * *